United States Patent

Gemmill, Jr. et al.

[11] 3,931,334
[45] Jan. 6, 1976

[54] LUBRICANT COMPOSITIONS COMPRISING SUBSTITUTED INDANS

[75] Inventors: Robert M. Gemmill, Jr., Woodbury; John W. Schick, Cherry Hill, both of N.J.

[73] Assignee: Mobil Oil Corporation, New York, N.Y.

[22] Filed: July 5, 1973

[21] Appl. No.: 376,485

Related U.S. Application Data

[62] Division of Ser. No. 125,853, March 18, 1971, Pat. No. 3,792,096, which is a division of Ser. No. 836,161, June 24, 1969, Pat. No. 3,640,870.

[52] U.S. Cl.............................................. 260/609 E
[51] Int. Cl.²..................................... C07C 149/00
[58] Field of Search .............................. 260/609 E

[56] References Cited
UNITED STATES PATENTS

| | | | |
|---|---|---|---|
| 2,968,678 | 1/1961 | Oswald | 260/609 E |
| 3,523,981 | 8/1970 | Gerhard et al | 260/668 |

*Primary Examiner*—Bernard Helfin
*Assistant Examiner*—Nicky Chan
*Attorney, Agent, or Firm*—Charles A. Huggett; Raymond W. Barclay; Benjamin I. Kaufman

[57] ABSTRACT

Lubricant compositions are provided comprising a substituted indan having the structure:

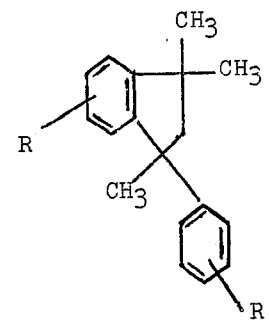

in which R is at least one member of the group consisting of hydrogen, alkyl, phenyl, carboxy alkyl, carboxy phenyl, phenoxy and their thiosubstituted derivatives. The method for the preparation of these substituted indans is also provided.

2 Claims, No Drawings

LUBRICANT COMPOSITIONS COMPRISING SUBSTITUTED INDANS

CROSS-REFERENCE TO RALATED APPLICATIONS

This is a division of application Ser. No. 125,853, filed Mar. 18, 1971, now U.S. Pat. No. 3,792,096, which in turn, is a division of application Ser No. 836,161 filed June 24, 1969, now U.S. Pat. No. 3,640,870.

BACKGROUND OF THE INVENTION

1. Field of the Invention

This invention relates to lubricant compositions, and, in one of its aspects, relates more particularly to lubricant compositions which are thermally and oxidatively stable and exhibit reduced tendency to deterioration. Still more particularly, in this aspect, the invention relates to such lubricant compositions as lubricant oils and greases, and also to other forms of organic media, in which these lubricants can be employed as blending stocks to modify their properties, for example such organic media as automatic transmission fluids, hydraulic fluids, heat-exchange fluids, and the like, in which the aforementioned stability against thermal and oxidative deterioration is an important requisite.

2. Description of the Prior Art

The importance of maintaining thermal and oxidative stability in lubricant compositions, for example in such representative areas as hydrocarbon lubricant oils and greases, or in any of the other aforementioned areas, is well known. Prior to the present invention, various lubricants or lubricant additives have been suggested for such purposee but have not been found to provide the desired degree of improvement. In some aspects either, or both, oxidative stability and thermal stability have not been significantly improved in the aforementioned compositions. In other instances, lubricants or lubricant additives employed for such purpose have proved to be costly, far outweighing the degree of improvement obtained.

SUMMARY OF THE INVENTION

In accordance with the present invention, as more fully hereinafter described, improved lubricants are provided which are thermally and oxidatively stable having the structure:

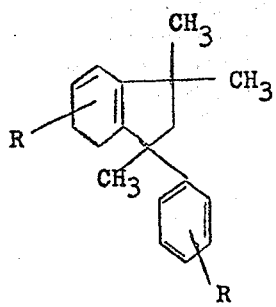

in which R is at least one member of the group consisting of hydrogen, alkyl, phenyl, carboxy alkyl, carboxy phenyl, phenoxy and their thiosubstituted derivatives.

These substituted indans, as more fully hereinafter described, have been found to be markedly effective not only in possessing thermal and oxidative stability as lubricants, per se, but also in imparting, as a blending stock, thermal and oxidative stability to lubricant compositions in the form of lubricant oils, greases and any of the aforementioned organic media such as automatic transmission fluids, hydraulic fluids, heat-exchange fluids and the like.

The organic compositions, of more specific importance, which are improved by blending with the substituted indans of the present invention may include mineral oils and synthetic oils of lubricating viscosities. Of particular significance is the improvement of petroleum distillate lubricating oils having boiling points as high as 650°F. or above and also mixtures of such oils. It should be noted, in this respect, that the term "distillate oils" is not intended to be restricted to straight-run distillate fractions. These distillate oils can be straight-run distillate oils, catalytically or thermally cracked (including hydrocracked) distillate oils, or mixtures of straight-run distillate oils, naphthas and the like, with cracked distillate stocks and may be of varying viscosities and pour points. Moreover, such oils can be treated in accordance with well-known commercial methods, such as acid or caustic treatment, hydrogenation, solvent-refining, clay treatment and the like.

As previously indicated, the aforementioned substituted indans may also be incorporated, as blending agents in lubricant vehicles of grease compositions. Such greases, may comprise a combination of a wide variety of lubricating vehicles and thickening or gelling agents. Thus, greases in which the aforementioned substituted indans are particularly effective as vehicle blending agents may comprise any of the conventional hydrocarbon oils of lubricating viscosity, as the oil vehicle, and may include mineral oils or mineral oils in combination with synthetic lubricating oils, aliphatic phosphates, esters and di-dester, silicates, siloxanes and oxalkyl ethers and esters. Mineral lubricating oils, preferably employed as the lubricating vehicle, may be of any suitable lubricating viscosity range from about 45 SSU at 100°F. to about 6,000 SSU at 100°F., and, preferably, from about 50 to about 250 SSU at 210°F. These oils may have viscosity indexes varying from below 0 to about 100 or higher. Viscosity indexes from about 70 to about 95 are preferred. The average molecular weights of these oils may range from about 250 to about 800. The lubricating oil is employed in the grease composition in an amount sufficient to constitute the balance of the total grease composition, after accounting for the desired quantity of the thickening agent, and other additive components to be included in the grease formulation.

As previously indicated, the oil vehicles employed in the novel grease formulations of the present invention, in which the aforementioned substituted indans are incorporated as blending agents, may comprise mineral oils or combinations of mineral oils with synthetic oils of lubricating viscosity. When high temperature stability is not a requirement of the finished grease, mineral oils having a viscosity of at least 40 SSU at 100°F., and particularly those falling within the range from about 60 SSU to about 6,000 SSU at 100°F. may be employed. In instances, where synthetic vehicles are employed in addition to mineral oils, as the lubricating vehicle, various compounds of this type may be successfully utilized. Typical synthetic vehicles include: polypropylene, polypropylene glycol, trimethylol propane esters, neopentyl and pentaerythritol esters, di-(2-ethyl hexyl) sebacate, di-(2-ethyl hexyl) adipate, dibutyl phthalate, fluorocarbons, silicate esters, silanes, esters of phosphorus-containing acids, liquid ureas, ferrocene derivatives, hydrogenated mineeral oils, chain-type polyphenyls, siloxanes and silicones (polysiloxanes), alkyl-substituted diphenyl ethers typified by a butyl-substituted bis (p-phenoxy phenyl) ether, phenoxy phenyl ethers, etc.

The lubricating vehicles of the aforementioned improved greases of the present invention containing the above-described substituted indans as blending agents, are combined with a grease-forming quantity of a thickening agent. For this purpose, a wide variety of materials may be employed. These thickening or gelling agents may include any of the conventional metal salts or soaps, which are dispersed in the lubricating vehicle in grease-forming quantities, in such degree as to impart to the resulting grease composition, the desired consistency. Other thickening agents that may be employed in the grease formation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any material which are normally employed for thickening or gelling hydrocarbon fluids for forming greases, can be used in preparing the aforementioned improved greases in accordance with the present invention.

The substituted indans of the present invention may be prepared, in general, by subjecting a mixture of an isopropyl aromatic compound and a halogen to a temperature sufficiently high to effect halogenation of the isopropyl group. Thereafter the halogenated isopropyl aromatic compound thus produced is subjected to elevated temperature, in the presence of an acidic catalyst, to an extent at which the halogenated isopropyl aromatic compound is converted to its corresponding substituted indan. In a preferred embodiment, the aforementioned halogenation is carried out at about room temperature, or below, but not lower than about 0°C. A preferred halogenation temperature range is from about 0°C. to about 10°C.

As previously indicated, the halogenated isopropyl aromatic compound is subjected to an elevated temperature at which this compound is converted to its corresponding substituted indan. In a preferred embodiment the halogenated isopropyl aromatic compound is subjected to an elevated temperature within the range from above the halogenation temperature employed, but not higher than the boiling point of the halogenated isopropyl aromatic compound. Preferably the halogenated isopropyl aromatic compound, for most purposes, is subjected to a temperature from about 100°C. to about 200°C. at which the corresponding substituted indan is produced.

As hereinbefore indicated, the halogenated isopropyl aromatic compound is subjected to elevated temperature, in the presence of an acidic catalyst, for conversion to the corresponding substituted indan. For this purpose any acidic material that has a ionization constant greater than about $1 \times 10^{-5}$, may be employed, and, exemplary thereof, are catalysts comprising a crystalline alumino-silicate zeolite catalyst in an amorphous silica-alumina matrix; sulfuric acid, trichloroacetic acid; monochloroacetic acid on the aforementioned alumino-silicate zeolite catalyst, phosphoric acid, nitric acid and other organic and inorganic acids having the aforementioned ionization constant.

DESCRIPTION OF SPECIFIC EMBODIMENTS

The following examples will serve to illustrate the novel substituted indans of the present invention, the method for their preparation and their utility in organic lubricating media.

EXAMPLE 1

Dimers of Monoisopropylbiphenyl

To a stirred pot containing 392 grams (2.0 moles) of monoisopropylbiphenyl and 1176 grams (15.1 moles) of benzene at a temperature between about 0°C. and about 10°C. was added dropwise 324 grams (2.03 moles) of bromine. A light source, comprising a 100 watt clear light bulb, was placed alongside the pot. After 10 hours, HBr evolution ceased, indicating completion of the reaction. The benzene was distilled off at reduced pressure leaving a quantitative yield of 551 grams of product. Upon analysis it was found that the molecular weight of the product was 275 (275 calculated) and the bromine content was 27.6% (29.1% calculated).

The dimerization was performed, employing 280 grams (1.0 mole of the above-described brominated product with 2.8 grams (1% by weight) of a crushed crystalline aluminosilicate zeolite catalyst in an amorphous silica-alumina matrix at 150°C. in a stirred flask for a period of 40 hours. The reaction was considered complete when successive samples showed no change by gas chromatographic analysis. The product (209.2 grams) was filtered in order to remove the catalyst and was dissolved in benzene. After washing the benzene solution to neutrality with water, the benzene was removed and the product was fractionally distilled under reduced pressure. Gas chromatography showed the product mixture to comprise 25%, by weight, of monoisopropylbiphenyl, 55–60% of the four expected isomeric dimers and 15–20% of polymer. Four isomeric dimers were the result of a di-isomeric monoisopropylbiphenyl charge stock. The chemical and physical properties obtained are hereinafter disclosed in Table I. The substituted indan, thus produced, can be depicted as having the structure:

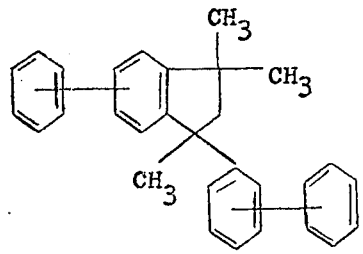

EXAMPLE 2

Codimers of Monoisopropylbiphenyl and Alpha-methyl Styrene 280 grams (1.0 mole) of the brominated monoisopropylbiphenyl from Example 1 was reacted with 118 grams (1.0 mole) of alpha-methyl styrene in the presence of 8.0 grams (2% by weight) of the acidic clay catalyst of Example 1 at a temperature of about 150°C.

in a stirred flask. After 47 hours, 331.8 grams (312 grams calculated) of the resulting product was recovered, in the manner described in Example 1. Gas chromatography showed unreacted monoisopropylbiphenyl (approximately 15% by weight), alpha-methyl styrene (approximately 24% by weight), the four expected codimers (approximately 37% by weight), and the four expected dimers of monoisopropylbiphenyl (approximately 24% by weight). The product mixture was then fractionally distilled at reduced pressure. The chemical and physical properties obtained are hereinafter disclosed in Table I. The substituted indan thus produced can be depicted as having the structure:

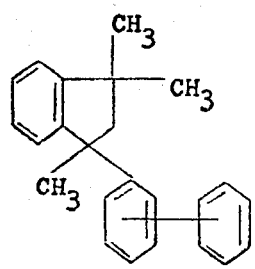

EXAMPLE 3

Dimers of Cumylphenylether (Phenoxy-cumene)

212 grams (1.0 mole) of cumylphenylether in 590 grams (7.6 moles) of benzene was brominated with 160 grams (1.0 mole) of bromine in the manner described in Example 1. The brominated product, following benzene removal, amounted to 308 grams (291 calculated) and had a molecular weight of 296 (291 calculated) and a bromine content of 26.2% (27.5% calculated). Dimerization of this material was carried out employing 154 grams (0.53 mole) of the brominated material and 4.6 grams (3%) of the acidic clay catalyst of Example 1 at a temperature of about 150°C. for a period of 16 hours. The resulting product was filtered and washed to neutrality. Gas chromatography showed the resulting product mixture to comprise approximately 49.0% cumylphenylether, 7.7% of a side product, 6.3% of the four expected dimers and 37.0% of polymer. Analysis of the side product (comprising approximately six components) showed an average molecular weight of 293 and a bromine content of 21.1%. The chemical and physical properties of the substituted indan product are hereinafter disclosed in Table I. The substituted indan thus produced can be depicted as having the structure:

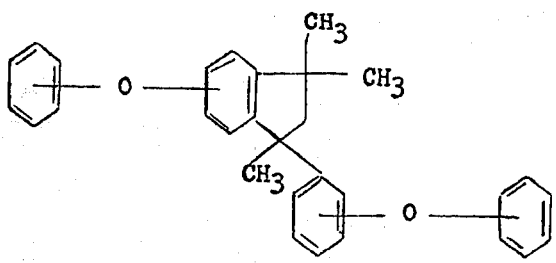

EXAMPLE 4

Monophenoxy-1,1,3-Trimethyl-3-Phenyl Indans

By following the procedure and the conditions of Example 3, 0.5 mole of cumylphenylether and 0.5 mole of cumene are brominated with 1.0 mole of bromine. The resulting product is found to comprise a mixture of 1,1,3-trimethyl-3-(phenoxy)phenyl indan and phenoxy-1,1,3-trimethyl-3-phenyl indan. The chemical and physical properties of these compounds are hereinafter disclosed in Table I. The substituted indans thus produced can be depicted as having the following structures:

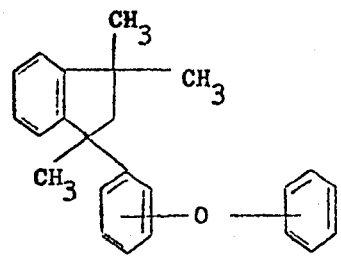

and

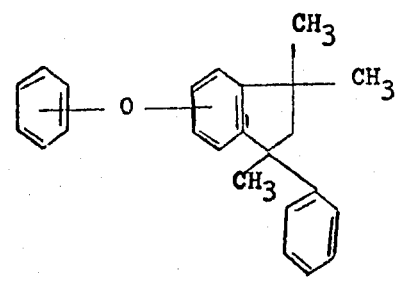

EXAMPLE 5

Codimer of Thiophenoxycumene and Cumene

A codimer of thiophenoxycumene and cumene can be prepared by substituting the same molar quantities fo thiophenoxycumene in place of cumylphenyl ether in Example 4 to produce a compound having the following properties:

|  | Calculated | Found |
|---|---|---|
| Molecular Weight | 344 | 344 |
| Carbon % | 83.72 | 82.11 |
| Hydrogen % | 6.98 | 6.76 |
| Oxygen % | 0 | 0.56 |
| Sulfur % | 9.30 | 9.80 |

The chemical and physical properties are hereinafter disclosed in Table I. The substituted indan thus produced can be depicted as having the structure:

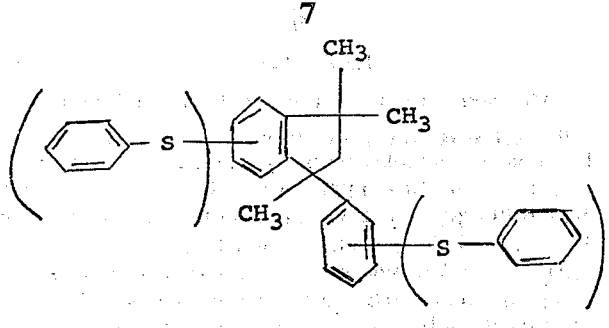

We claim:
1. A substituted indan having the structure:

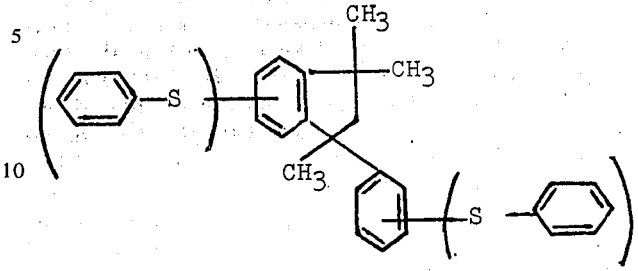

TABLE I

| | | Example 1 | Example 2 | Example 3 | Example 4 | Example 5 | |
|---|---|---|---|---|---|---|---|
| Molecular Weight | | 388 | 312 | 420 | 328 | 344 | |
| Bromine Content % | | 0.42 | 1.19 | (0.19) | (0.15) | 0) | |
| Chlorine Content % | | 0 | 0 | 0 | 0 | 0) | Sulfur |
| Bromine Number | | 0 | 0.6 | 0 | 0 | 0) | 9.2% |
| TAN | | 0 | 0 | 0 | 0 | 0) | |
| Flash, °F. | | 515 | 435 | 490 | 425 | 460 | |
| Fire, °F. | | 580 | 510 | 585 | 465 | 515 | |
| Pour, °F. | | +120 | +65 | +60 | +45 | +45 | |
| KV 100°F. | | Solid | 3806 | 19571 | 400.9 | 468.9 | |
| KV 210°F. | | 130 | 14.68 | 28.66 | 9.10 | 9.86 | |
| KV 400°F. | | | 1.55 | | 1.40 | | |
| AIT, °F. | | 830 | 810 | 875 | 870 | 830 | |
| Thermal Stability | % Loss | 0.007 | 0.003 | 0.086 | 0.010 | 0.13 | |
| 785°F., 90 min. | KV 100°F. | | 4020 | | | 454.3 | |
| | KV 210°F. | 131.5 | 14.94 | 28.40 | 8.40 | 9.79 | |
| | TAN | 0 | 0.08 | 0.31 | 0.49 | 0.04 | |
| Ox./Corr. 450°F. | ΔKV % 100°F. | | | | 18.3 | Crystallized | |
| | ΔKV % 210°F. | 2900 | 184 | 4.3 | 6.0 | in pure form | |
| | TAN | 2.1 | 3.7 | 0.22 | 0.44 | after several | |
| | Sludge | 0 | Trace | 0 | 0 | days. | |
| Corrosion | Al | | | 0 | 0 | | |
| mg/cm² | Ag | +0.2 | −1.0 | −0.1 | −0.1 | | |
| | Cu | −0.3 | −4.1 | −0.2 | −0.4 | | |
| | Mg | Trace | Trace | −0.5 | 0 | | |
| | Steel | −0.1 | −5.1 | 0 | 0 | | |
| | Ti | | | 0 | | | |
| | Bronze | | | 0 | | | |
| Ox.Corr. 450°F. | ΔKV % 100°F. | | | | 20.7 | | |
| No Metals | ΔKV % 210°F. | | 79.0 | | 6.1 | | |
| | TAN | 3.3 | 7.7 | | 0.51 | | |
| | Sludge | 0 | 0 | | 0 | | |

From the foregoing data and examples, it will be apparent that the novel substituted indans of the present invention possess chemical and physical characteristics which make them particularly adaptable for use as lubricants, per se, or as blending materials having a wide variety of lubricant compositions for imparting thermal and oxidative stability. Although the present invention has been described herein by means of certain specific embodiments and illustrate examples, it is not intended that the scope thereof be limited in any way, and is capable of various modifications and adaptations, as those skilled in the art will readily appreciate.

2. A process for producing the indan of claim 1 which comprises subjecting a mixture of a thiophenoxycumene compound and a halogen to a temperature from about 0°C to about 20°C to effect halogenation of the isopropyl group of said cumene compound; and thereafter subjecting the halogenated cumene compound thus produced to a temperature from about 100°C to about 200°C in the presence of an acidic catalyst having an ionization contant greater than about $1 \times 10^{-5}$ to an extent at which the aformentioned compound is converted to its corresponding indan.

* * * * *